(12) United States Patent
Wang et al.

(10) Patent No.: US 8,986,683 B2
(45) Date of Patent: Mar. 24, 2015

(54) COMBINED USE OF RIBONUCLEASE AND ARTEMISININ

(75) Inventors: Qingcheng Wang, Shanghai (CN); Ruling Shen, Shanghai (CN); Jun Li, Shanghai (CN); Jian Fei, Shanghai (CN); Zhugang Wang, Shanghai (CN)

(73) Assignees: Shanghai Biomodel Organism Science & Technology Co., Ltd., Shanghai (CN); Shanghai Research Center for Model Organisms, Shanghai (CN)

( * ) Notice: Subject to any disclaimer, the term of this patent is extended or adjusted under 35 U.S.C. 154(b) by 110 days.

(21) Appl. No.: 13/608,077

(22) Filed: Sep. 10, 2012

(65) Prior Publication Data

US 2013/0052181 A1    Feb. 28, 2013

Related U.S. Application Data

(63) Continuation-in-part of application No. PCT/CN2011/071607, filed on Mar. 8, 2011.

(30) Foreign Application Priority Data

Mar. 8, 2010  (CN) .......................... 2010 1 0119612

(51) Int. Cl.
| | | |
|---|---|---|
| A61K 38/46 | (2006.01) | |
| A61K 38/47 | (2006.01) | |
| A61K 31/335 | (2006.01) | |
| A61K 31/35 | (2006.01) | |
| A61K 31/366 | (2006.01) | |
| A61K 31/357 | (2006.01) | |
| A61K 31/352 | (2006.01) | |
| C12N 9/16 | (2006.01) | |
| A61K 45/06 | (2006.01) | |
| C12N 5/09 | (2010.01) | |
| A61K 9/00 | (2006.01) | |

(52) U.S. Cl.
CPC ............. *A61K 31/366* (2013.01); *A61K 31/335* (2013.01); *A61K 31/357* (2013.01); *A61K 31/352* (2013.01); *C12N 9/16* (2013.01); *A61K 45/06* (2013.01); *A61K 38/465* (2013.01); *C12N 5/0693* (2013.01); *A61K 9/0019* (2013.01); *C12N 2501/70* (2013.01)
USPC .......................... 424/94.6; 514/451; 514/452

(58) Field of Classification Search
CPC .............. A61K 2300/00; A61K 45/06; A61K 31/7105; A61K 31/366; A61K 31/58; A61K 31/357; A61K 31/352; C12N 9/22; C12N 1/00; C12N 9/00; C07C 51/412
See application file for complete search history.

(56) References Cited

U.S. PATENT DOCUMENTS

| | | | |
|---|---|---|---|
| 2007/0213360 A1* | 9/2007 | Pekari et al. ................... | 514/301 |
| 2008/0161324 A1 | 7/2008 | Johansen et al. | |
| 2010/0279976 A1* | 11/2010 | Wang et al. ..................... | 514/49 |

FOREIGN PATENT DOCUMENTS

WO    2007/096395    8/2007

OTHER PUBLICATIONS

Costanzi et al., Cancer Investigation, 23:643-650, 2005.*
International Search Report from international application No. PCT/CN2011/071607, dated Jun. 16, 2011 (8 pages).

* cited by examiner

*Primary Examiner* — Jennifer McDonald
*Assistant Examiner* — Qing Xu
(74) *Attorney, Agent, or Firm* — Hamre, Schumann, Mueller & Larson, P.C.

(57) ABSTRACT

The invention discloses a kit which comprises a formulation containing artemisinin or the derivatives thereof, a formulation containing ribonuclease, and a specification.

8 Claims, 3 Drawing Sheets

(a)

| Abbreviation of Biochemical Index | Full Name |
|---|---|
| CRE | Creatinine |
| BUN | Blood Urine Acid |
| TP | Total Protein |
| GLOB | Globulin |
| T-BIL | Total Bilirubin |
| ALT | Alanine Aminotransferase |
| AST | Aspartate Aminotransferase |
| ALB | Albumin |

(b)

COMBINED USE OF RIBONUCLEASE AND ARTEMISININ

FIELD OF THE INVENTION

The invention relates to the oncotherapy, especially the combined use of ribonuclease and artemisinin.

BACKGROUND OF THE INVENTION

Onconase is one kind of ribonucleases in ova or early embryos of *Rana pipiens*. It comprises 104 amino acid residues and has a molecular weight of about 12,000 daltons. Onconase is a member of RNase A (Bovine pancreatic ribonuclease A) super family. Onconase has a 30% identity to RNase A in primary structure and both of them have a quite similar tertiary structure. Onconase can inhibit growth of various tumors. Although Onconase is a protein drug, it is low immunogenic so that it is clinically suitable for multiple courses of treatment. It can counteract the multiple drug resistance and has few side effects.

Artemisinin was invented and developed as a novel anti-malaria drug by Chinese scientists. Considering the common drug resistance of quinine drugs, artemisinin and derivatives thereof have replaced them and become main drugs for anti-malaria over the world. Artemisinin is a sesquiterpene lactone compound extracted from leaves of *artemisia annua*, which is a Chinese medicinal plant. The Endoperoxide Bridge in the macro-ring of artemisinin releases carbon-centered free radicals under ferrous iron and ferroheme catalysis. The cells may die after alkylation of intracellular protein and nuclear acid caused by these free radicals. The plasmodia parasitizing in red blood cells contain a large amount of ferroheme derived from hemoglobin so that artemisinin is easily activated and kill plasmodia. Artemisinin or derivatives thereof, such as dihydroartemisinin, artemether, arteether, and artesunate etc., have already been widely used for malaria treatments. More artemisinin derivatives are under development. Scientists in China and overseas have found out that artemisinin has an antitumor effect in recent years. Artemisinin or the derivatives thereof presents a broad-spectrum antitumor effect.

However, it is unknown in the art about the effect of combination of these two unique drugs of ribonuclease and artemisinin for tumor treatments. Such a problem is eagerly to be solved in the field.

SUMMARY OF THE INVENTION

The purpose of the present invention is to provide a method for anti-tumor treatment with the combination of ribonuclease and artemisinin or derivatives thereof.

In the first aspect, the invention provides a kit which comprises:
 a formulation containing artemisinin or the derivatives thereof;
 a formulation containing ribonuclease; and
 a specification.

The formulation containing artemisinin or the derivatives thereof in the kit comprises tablet, capsule, suppository, and intravenous injection; and the formulation containing ribonuclease comprises intravenous injection.

In the second aspect, the invention provides an in vitro non-therapeutic method for inhibiting growth of a tumor cell, comprising:
 (1) mixing tumor cells with ribonuclease and culturing tumor cells (2,000~4,000 cells per well, preferably 2,500~3,500 cells per well, and more preferably 3,000 cells per well) for 20~30 hours;
 (2) adding artemisinin or the artemisinin derivatives and further culturing for 20~50 hours; and
 (3) detecting the cytotoxicity by a MTT method.

The concentration of the ribonuclease is 0.12~0.6 μmol/L, based on the total volume of the mixture of tumor cells and ribonuclease. The concentration of artemisinin or the derivatives thereof is 2~10 μmol/L, based on total volume of the mixture of tumor cells, ribonuclease, and artemisinin or the derivatives thereof.

In the third aspect, the invention provides an experimental and therapeutic method for tumor treatment, which comprises:
 (a) intravenously administrating a formulation containing ribonuclease to a subject such as a nude mice inoculated with tumor subcutaneously, and in a dosage of 0.5~5 mg/kg if Onconase is used;
 (b) 20~30 hours after step (a), administrating a formulation containing artemisinin or the derivatives thereof to the subject having tumor and in a dosage of 5~50 mg/kg if DHA is used;
 (c) 40~60 hours after step (b), repeating step (a); and
 (d) 20~30 hours after step (c), repeating the step (b).

In the therapeutic method, the formulation containing artemisinin or the derivatives thereof comprises tablet, capsule, suppository, and intravenous injection; and the formulation containing ribonuclease comprises intravenous injection.

In the fourth aspect, the invention provides a method for co-administrating ribonuclease and artemisinin or the derivatives thereof so as to sufficiently exert their efficacy. The method comprises:
 administrating an effective amount of artemisinin or the derivatives thereof 20~30 hours after an effective amount of ribonuclease is administrated.

Accordingly, it has been demonstrated in the invention that there is a remarkable synergy for treating tumor when combining ribonuclease with artemisinin or the derivatives thereof. Both of them are antitumor drugs with low toxicity, low immunogenicity, and broad spectrum. The combination of these two drugs strengthens their antitumor activity while reducing the side effects, thus making it a novel and promising means for tumor treatment.

DESCRIPTION OF FIGURES OF THE INVENTION

FIG. 1(*b*) shows analysis on equivalent effect for treating 3,000 MSTO-211H cells per well with Onc and DHA for 72 hours.

Figure 3:
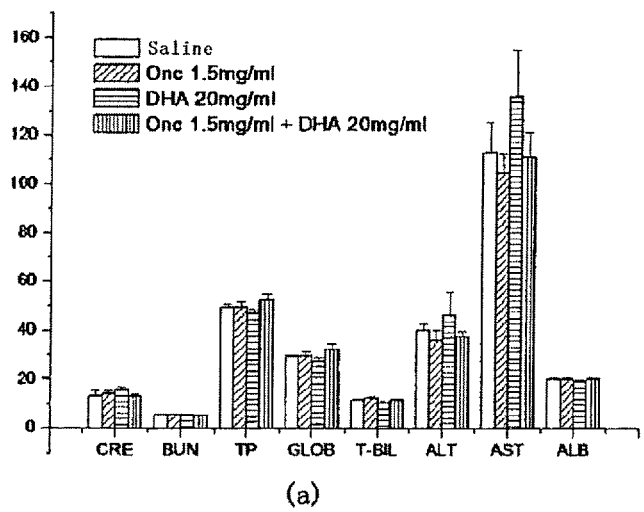

FIG. 3 shows the results of blood biochemical index of the nude mice with tumor. FIG. 3(*a*) is a bar chart that shows: Group Saline (Saline, n=6), Group Onc (Onc=1.5 mg/kg, n=5), Group Onc+DHA (Onc 1.5 mg/kg+DHA 20 mg/kg, n=5), Group DHA (DHA=20 mg/kg, n=5); while each unit of Y-axis of the chart represents CREk-μmol/L, BUN-mmol/L, TP-g/L, GLOB-g/L, T-BIL-μmol/L, ALT-U/L, AST-U/L, ALB-U/L. FIG. 3(*b*) shows the corresponding full name of each index.

Figure 4:
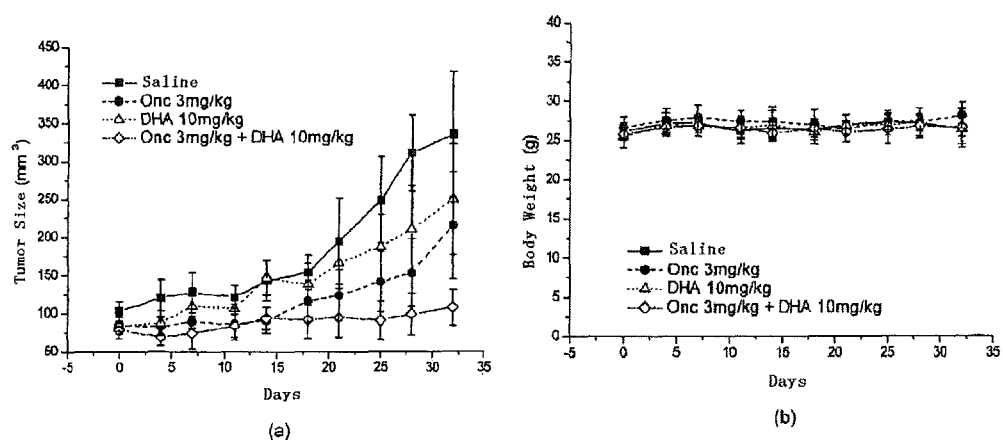

FIG. 4 shows that the co-administration of Onc and DHA significantly reduced tumor size in nude mice which were inoculated with lung cancer cell A549. FIG. 4(a) and FIG. 4(b) show the inhibition of tumor size and the body weight variation of mice at corresponding periods after co-administration.

DETAILED DESCRIPTION OF THE INVENTION

After comprehensive and intensive studies, the inventors have discovered that combined administration of ribonuclease and artemisinin or the derivatives thereof results in remarkable synergistic effects both in vivo and in vitro. Specifically, the example comprises Onconase and the dihydroartemisinin (DHA), and Onconase should be used prior to DHA. The inventor completed the present invention based on the discovery.

As used herein, the term "ribonuclease" refers to a kind of ribonuclease with cytotoxicity and comprises Onconase (Onc or Ranpimase), RNase from *Rana catesbiana* or *Rana chensinensis*, bovine sperm tube RNase, neurotoxin derived from human eosinophilic cells, as well as any genetic-engineered bovine pancreas RNase or human pancreas RNase, etc. Onc is preferable.

Onconase is a kind of enzyme effective for inhibition of tumor, and it can degrade tRNAs selectively in the cytoplasm and inhibit protein synthesis, thereby inhibiting cell proliferation and inducing apoptosis.

In the present invention, Onconase suitable for use can be naturally available. For example, it can be isolated or purified from animals. Furthermore, said Onconase can be synthesized. For example, a recombined Onconase can be produced according to conventional genetic engineering technology. The recombined Onconase is preferably used in the invention.

Any suitable Onconase can be used in the invention. Said Onconase comprises a full-length Onconase or any biologically active fragments thereof. Preferably, the amino acid sequence of Onconase is essentially the same as that of SEQ ID NO: 4.

The invention also comprises any amino acid sequence of Onconase which has a substitution, deletion or insertion of one or more amino acid residues. Onconase or its biologically active fragments may comprise some substituted sequence for conserved amino acids, and said substituted sequence does not change Onconase activity or remains partial Onconase activity. The suitable substitution of amino acid is a known technique in the art, which can be easily carried out to maintain the biological activity of molecule. These techniques enable those skilled in the art to realize that, generally, a change of single amino acid in a non-essential domain of a polypeptide will essentially not alter biological activity. See Watson et al., Molecular Biology of The Gene (4$^{th}$ version), The Benjamin/Cummings Pub. Co., 1987, P 224.

Any biologically active fragments of Onconase can be used in the invention. As used herein, the biologically active fragment of Onconase means a polypeptide that remains partial or all activity of the full-length Onconase. Normally, said biologically active fragment remains at least 50% of the activity of full-length Onconase. More preferably, said biologically active fragment remains at least 60%, 70%, 80%, 90%, 95%, 99%, or 100% of the full-length Onconase activity.

Any modified or improved Onconase can also be used in the invention, e.g., those modified or improved for prolonging half-life, for improving stability, or for enhancing the ability to kill tumor cells. Although the modified or improved Onconases or the genes thereof have certain differences from those naturally-occurring, they can still kill tumor cells and bring no undesired side effect or toxicity. In other words, any alternative form can be used in the invention as long as it does not influence the biological activity of Onc or biological function of Onc gene.

As an embodiment, the Onconase is expressed by recombinant. The encoding gene for Onc has a full-length of 315 bp, encodes a polypeptide having 104 amino acids. The gene has the sequence of SEQ ID NO: 3 and the polypeptide has the sequence of SEQ ID NO: 4.

Onconase can be produced by using a conventional genetic engineering technology which comprises:

(1) transforming or transfecting a suitable host cell with a recombinant expression vector containing a gene encoding Onconase;

(2) culturing the host cell in a proper medium;

(3) isolating or purifying the protein of interest from the culture or the cells.

As used herein, the term "artemisinin or the derivatives thereof" refers to dihydroartemisinin (DHA), artesunate, artemether, dihydroartemether and arteether, etc, and preferably, DHA.

Several structures of artemisinin or the derivatives thereof known in the art are shown as followed:

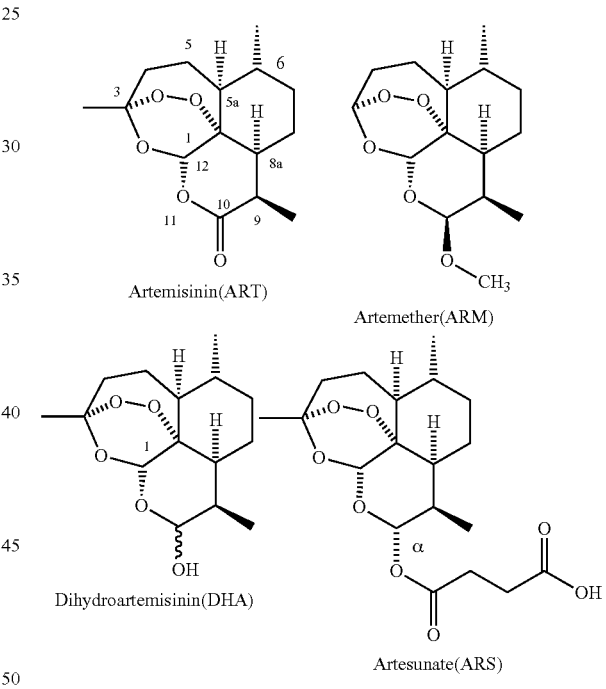

As used herein, the term "the derivatives thereof" includes not only those mentioned herein, but also the derivatives which remain artemisinin activity after modifying side chain groups in the backbone through simplified chemical methods such as substitution or reduction by those skilled in the art. The preparation methods for these derivatives are available in the textbooks in the art. Besides, the derivatives thereof also contain various salts of acid and base, hydrates, and optical isomers.

The invention provides a kit which comprises:
a formulation containing artemisinin or the derivatives thereof;
a formulation containing ribonuclease; and
a specification.

The formulation containing artemisinin or the derivatives thereof in the kit comprises tablet, capsule, suppository, and intravenous injection; and the formulation containing ribonuclease comprises intravenous injection.

The formulation comprising artemisinin or the derivatives thereof can be a unit dosage form comprising artemisinin or the derivatives thereof. The formulation comprising ribonuclease can be a unit dosage form comprising ribonuclease.

The kit has two or more unit dosage forms containing artemisinin or the derivatives thereof and two or more unit dosage forms containing ribonuclease respectively; preferably, the kit has 4~10 unit dosage forms for each active ingredient respectively.

As used herein, the term "unit dosage forms" refers to a formulation prepared from the composition for a single dose, which includes, but is not limited to, various forms for solid (such as tablets), liquid, capsule, and sustained releasing form.

The unit dosage forms containing artemisinin or the derivatives thereof include tablet, capsule, suppository, and intravenous injection; and the unit dosage forms containing ribonuclease is intravenous injection.

The specification provided according to the invention contains a description of usage, such as the following: the use of the kit is to administrate the dosage unit comprising artemisinin or the derivatives thereof 20~30 hours after the administration of the dosage unit comprising ribonuclease; and the procedure can be repeated q.o.d (every other day).

The kit provided by the invention can be prepared according to the following step: putting the specification together with a formulation containing artemisinin or the derivatives thereof and a formulation containing ribonuclease together, thereby forming a kit. Preferably, said formulation containing artemisinin or the derivatives thereof is a unit dosage form containing artemisinin or the derivatives thereof, and said formulation containing ribonuclease is a unit dosage form containing ribonuclease. In said step, it is preferred to put the specification together with two or more unit dosage forms containing artemisinin or the derivatives thereof and two or more unit dosage forms containing ribonuclease, thereby forming the kit.

The kit provided by the invention is useful for tumor treatments. The tumor includes malignant mesothelioma, non-small-cell lung cancer, pancreatic cancer, nasopharyngeal cancer, thymoma, rectal cancer, breast cancer, melanoma, kidney cancer, leukemia, and lymphoma, etc. and preferably, malignant mesothelioma and non-small-cell lung cancer.

The invention provides an in vitro non-therapeutic method for inhibiting growth of a tumor cell. Said method comprises:

(1) mixing the tumor cells with the ribonuclease and culturing the tumor cells for 20-30 hours; and (2) adding artemisinin or the artemisinin derivatives and further culturing for 45~50 hours.

The tumor cells include cells of malignant mesothelioma, non-small-cell lung cancer, pancreatic cancer, nasopharyngeal cancer, thymoma, rectal cancer, breast cancer, melanoma, kidney cancer, leukemia, and lymphoma, etc. and preferably, cells of malignant mesothelioma or non-small-cell lung cancer.

In step (1), mix 3000 tumor cells per well with ribonuclease at a concentration of $1.2~6\times10^{-1}$ μmol/L and culture the tumor cells for 20~30 hours.

In step (2), the concentration of the artemisinin or the derivatives thereof is 2~10 μmol/L.

The duration of the culture in step (1) is preferably 22~26 hours; and the duration of the further culture in step (2) is preferably 46~48 hours.

The formulation containing artemisinin or the derivatives thereof comprises tablet, capsule, suppository, and intravenous injection; and the formulation containing ribonuclease comprises intravenous injection.

Preferably, the formulation containing artemisinin or the derivatives thereof is a unit dosage form containing artemisinin or the derivatives thereof, and said formulation containing ribonuclease is a unit dosage form containing ribonuclease.

The unit dosage form containing artemisinin or the derivatives thereof may include tablet, capsule, suppository, and intravenous injection.

The unit dosage form containing ribonuclease includes intravenous injection.

The duration in step (b) and (d) is preferably 22~26 hours; and the duration in step (c) is preferably 45~50 hours.

The tumor cells include cells of malignant mesothelioma, non-small-cell lung cancer, pancreatic cancer, nasopharyngeal cancer, thymoma, rectal cancer, breast cancer, melanoma, kidney cancer, leukemia, and lymphoma, etc. and preferably, cells of malignant mesothelioma or non-small-cell lung cancer.

The features of the present invention mentioned above, or the features mentioned in the examples, can be combined at will. Any feature disclosed in the present specification can be used in combination with any other features, and each feature disclosed in the specification can be replaced with an alternative feature which can serve an identical, equivalent, or similar purpose. Therefore, the features disclosed herein are only general exemplary examples for any equivalent or similar features, unless specifically indicated otherwise.

The main advantages of the invention include:

1. The effect of tumor growth inhibition is enhanced by combining Onc with DHA.

2. The side effects of the two drugs are not exactly the same and side effects are reduced because the dosage of each drug is reduced when they are co-administrated.

3. Onc and DHA are drugs with low toxicity and immunogenicity and those properties are maintained in the combination of the two drugs so that the combination can possibly be used for a long term.

4. DHA has a great ability to inhibit angiogenesis of tumors, so does Onc. The combination of the two drugs can prevent or avoid the recurrence of tumors after chemotherapy or radiotherapy.

5. The kit comprising the two drugs enables the dose of each course, the schedule and the proportion of two drugs so that the treatment can be carried out conveniently and safely.

The present invention will be further illustrated below with reference to specific examples. It should be understood that these examples are only to illustrate the present invention but not to limit the scope of the present invention. The experimental methods with no specific conditions described in the following examples are generally performed under conventional conditions, such as the conditions described in Sambrook et al, Molecular Cloning: the Laboratory Manual (New York: Cold Spring Harbor Laboratory Press, 1989), or according to the manufacture's instruction. Unless indicated otherwise, all of the percentages and parts are calculated by weight.

The unit of weight-to-volume ratio in the invention is well known by those skilled in the art. For instance, it refers to the solute weight in the solution of 100 ml.

Unless indicated otherwise, all the specific and scientific terms used herein are understood as those terms known by the skilled in the art. Furthermore, any methods or materials which are equivalent or similar to the content herein could be used in the invention. The preferred embodiments and materials in the invention are exemplary only.

Example 1

Cytotoxic Effect of Co-Administration of Onc and DHA on Malignant Mesothelioma MSTO-211H Cells Malignant mesothelioma MSTO-211H cells were incubated in RPMI1640 (GIBICO) culture medium containing 10% fetal calf serum, penicillin (100 units/ml), and streptomycin (100 μg/ml). 90 μl of culture medium ($2 \times 10^4$ cells/ml) was added into each well of a 96-well plate and culture was conducted in a $CO_2$ (5%) incubator for 12 hours. 10 μl of Onc protein samples having a predetermined concentration gradient was added into co-administration well, and Onc, DHA or PBS were totally added into different control wells individually. After 24 hours, DHA (10 μl) having a predetermined concentration gradient was added into co-administration well. After culturing 48 hours, the cell viability was detected by a MTT assay; and the co-administration effect was determined using drug-equivalent-line principle. The result is shown in FIG. 1.

The highest administration concentration of Onc is [10A]= 0.6 μmol/L, and the highest administration concentration of DHA is [10B]=10 μmol/L. The dilutions were prepared in accordance with a certain gradient at the ratio of A/B=5/0, 4/1, 3/2, 2/3, 1/4, 0/5. Onc was first added. After 24 hours, the prepared DHA solution was added. The protein concentration vs cell viability profile for each ratio of combination was obtained (FIG. 1(a)), and the $IC_{50}$ for Onc and DHA in each ratio of composition were calculated. Using Onc value of each ratio as the X-axis, and DHA value as the Y-axis to form a two-dimensional plot. When connecting the coordinate points of ratio [5/0] and [0/5], since the remaining four points are in the left side of the line, the results shows that the co-administration of Onc and DHA has synergistic effects on malignant mesothelioma MSTO-211H (FIG. 1(b)).

Figure 1:
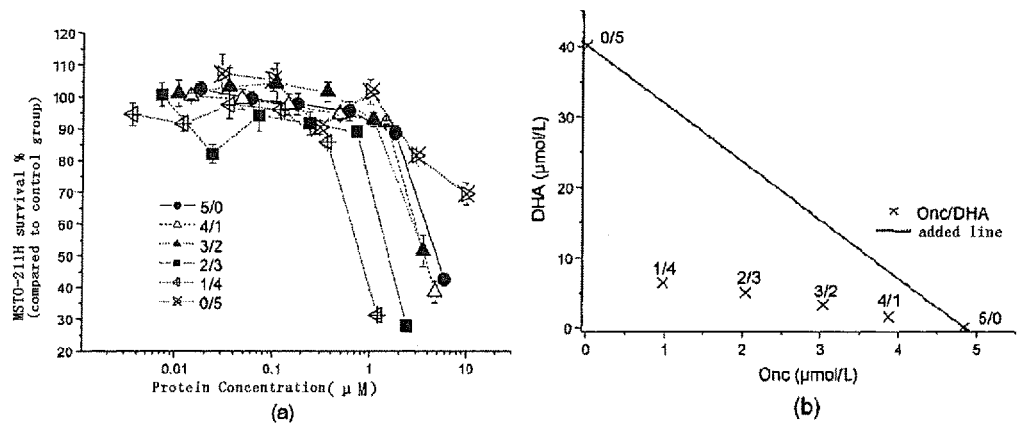
FIG. 1 shows that combination of Onc and DHA has a antitumor effect on malignant mesothelioma cell MSTO-211H, wherein FIG. 1(*a*) is the curve of protein concentration vs. cell survival rate.

FIG. 1 shows the synergistic anti-tumor effects of Onc and DHA on malignant mesothelioma MSTO-211H cell. The highest administration concentration of Onc is [10A]=0.6 umol/L, and the highest administration concentration of DHA is [10B]=10 μmol/L. The dilutions were prepared in accordance with a certain gradient at the ratio of A/B=5/0, 4/1, 3/2, 2/3, 1/4, 0/5. Onc was first added. After 24 hours, the prepared DHA solution was added and the incubation was continued for 48 hours. The protein concentration vs cell viability profile for each ratio of combination was obtained (FIG. 1(a)), and the $IC_{50}$ for Onc and DHA in each ratio of composition were calculated. Using Onc value of each ratio as the X-axis, and DHA value as the Y-axis to form a two-dimensional plot. When connecting the coordinate points of ratio [5/0] and [0/5], since the remaining four points are in the left side of the line, the results shows that the co-administration of Onc and DHA has synergistic effects on malignant mesothelioma MSTO-211H (FIG. 1(b)).

Example 2

Co-Administration of Onc and DHA to Treat Nude Mice Inoculated with Malignant Mesothelioma MSTO-211H A sufficient quantity of malignant mesothelioma MSTO-211H cells were collected. 100% Matrigel was added and mixed with the cells. $2 \times 10^6$ tumor cells were inoculated under the epidermal of right hind limb of every nude mouse. The administration was started on the tenth day after inoculation. In the co-administration group, Onc was injected at a dosage of 1.5 mg/kg in the tail vein twice every week, and DHA was injected intraperitoneally at a dosage of 20 mg/kg on the next day, totally three weeks (6 times). In the control groups, 1.5 mg/kg of Onc was injected in the tail vein, or 20 mg/kg of DHA was injected intraperitoneally, or saline was injected. The administration was twice a week, totally for three weeks (6 times). Measure the diameter of the tumor twice every week, count the volume of tumor according to the volume of tumor=0.4×length×width², and record the body weight of mice. The result is shown in FIG. 2.

Figure 2:
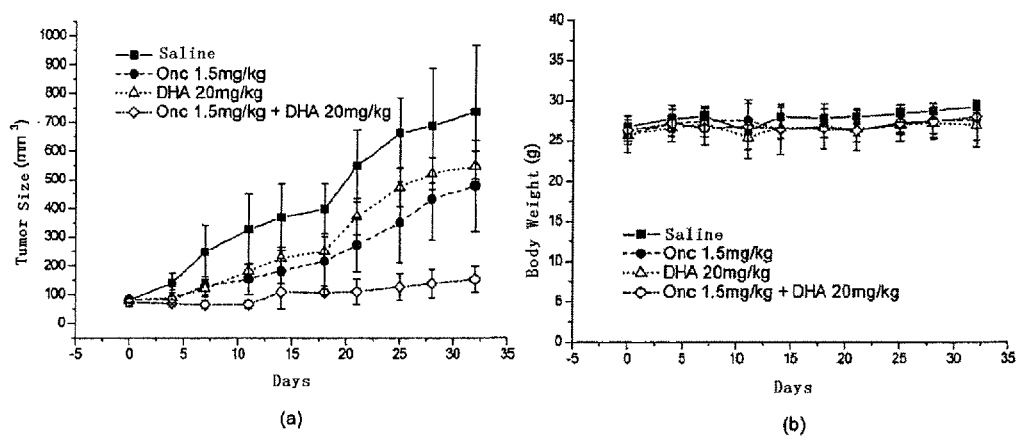
FIG. 2 shows that the co-administration of Onc and DHA significantly reduced tumor size in nude mice which were inoculated with MSTO-211H cells; wherein FIG. 2(*a*) and FIG. 2(*b*) show the inhibition of tumor size and the body weight variation of mice at corresponding periods after administration.

FIG. 2 shows that synergistic administration of Onc and DHA can significantly reduce the volume of tumor in malignant mesothelioma MSTO-211H tumor-bearing nude mice. FIGS. 2(a) and 2(b) show the inhibition of tumor volume after administration and the change of mice body weight at the corresponding periods (saline group: saline, n=6; Onc administration group: Onc 1.5 mg/kg, n=5; DHA administration group: DHA 20 mg/kg, n=5; co-administrated group: Onc 1.5 mg/kg+DHA 20 mg/kg, n=5).

The result shows that the anti-tumor effect of combination of two drugs is significantly stronger than that of either drug, and it can almost entirely inhibit the growth of tumor. The combination of two drugs does not cause significant change of nude mice's body weight, which means that the drugs are of low toxicity. FIG. 2b shows the changes in body weight of nude mice after administration. If body weight was significantly decreased, it indicates that the drugs may be toxic; if the body weight does not change significantly, it indicates that the drugs have low toxicity.

Example 3

Blood Biochemical Index Detection of Liver and Kidney Damage Condition of Tumor-Bearing Nude Mice after Administration On the tenth day after administration was stopped, 500 μl blood sample was taken from the eye, centrifuged and 200 μl serum was obtained. The biochemical index of serum was determined. The results are shown in FIG. 3.

FIG. 3 shows the analysis of blood biochemical index of tumor-bearing nude mice: saline group (saline, n=6), Onc administration group (Onc=1.5 mg/kg, n=5), co-administration group (Onc 1.5 mg/kg+DHA 20 mg/kg, n=5), DHA administration group (DHA=20 mg/kg, n=5). The unit of Y-axis of every index are: CRE-μmol/L; BUN-mmol/L; TP-g/L; GLOB-g/L; T-BIL-μmol/L; ALT-U/L; AST-U/L; ALB-g/L (FIG. 3(a)). FIG. 3(b) shows the corresponding full name of each index.

The result shows that most indexes do not have any changes of statistical significance, only the GLOB of the administration groups is significantly higher than the control group. It may be caused by the inflammation which was caused by tumor necrosis due to the drug administration.

Example 4

Co-Administration of Onc and DHA to Treat Nude Mice Inoculated with Non-Small Cell Lung Cancer A549

A sufficient quantity of non-small cell lung cancer A549 cells were collected. 100% Matrigel was added and mixed with the cells. $5 \times 10^6$ tumor cells were inoculated under the epidermal of right hind limb of every nude mouse. The administration was started on the tenth day after inoculation. In the co-administration group, Onc was injected at a dosage of 3 mg/kg in the tail vein twice every week, and DHA was injected intraperitoneally at a dosage of 10 mg/kg on the next day, totally three weeks (6 times). In the control groups, 3 mg/kg of Onc was injected in the tail vein, or 10 mg/kg of DHA was injected intraperitoneally, or saline was injected. The administration was twice a week, totally for three weeks (6 times). Measure the diameter of the tumor twice every week, count the volume of tumor according to the volume of tumor=0.4×length×width$^2$, and record the body weight of mice. The result is shown in FIG. 4.

FIG. 4 shows that synergistic administration of Onc and DHA can significantly reduce the volume of tumor in lung cancer A549 cell tumor-bearing nude mice. FIGS. 4(a) and 4(b) show the inhibition of tumor volume after administration and the change of mice body weight at the corresponding periods (saline group: saline, n=5; Onc administration group: Onc 3 mg/kg, n=5; DHA administration group: DHA 10 mg/kg, n=5; co-administrated group: Onc 3 mg/kg+DHA 10 mg/kg, n=5).

The result shows that the anti-tumor effect of combination of two drugs is significantly stronger than that of either drug, and it can almost entirely inhibit the growth of tumor. The combination of two drugs does not cause significant change of nude mice's body weight, which means that the drugs are of low toxicity. FIG. 4b shows the changes in body weight of nude mice after administration. If body weight was significantly decreased, it indicates that the drugs may be toxic; if the body weight does not change significantly, it indicates that the drugs have low toxicity.

The above examples are merely preferred examples of the invention, which are not used to limit the technical scope of the invention which is defined by the appended claims. If any technical solutions or methods made by others are identical to those defined in the appended claims, or are substantially equivalent, these equivalents still fall within the scope as defined by the appended claims.

The invention claimed is:

1. A kit for treating tumors, consisting of:
a formulation containing an artemisinin derivative;
a formulation containing ribonuclease; and
a specification,
wherein the artemisinin derivative and the ribnuclease are the only active ingredients contained in the kit for treating the tumors, where (1) the artemisinin derivative and (2) the ribonuclease are present in amounts effective for treating a tumor in a subject in need thereof,
wherein the artemisinin derivative is artemether, dihydroartemisinin, artesunate, arteether or dihydroartemether.

2. The kit of claim 1, wherein the formulation containing the artemisinin derivative is in the form of a tablet, a capsule, a suppository preparation, or an injection preparation; and the formulation containing ribonuclease is in the form of an injection preparation.

3. The kit of claim 1, wherein the tumor is at least one selected from the group consisting of pancreatic cancer, nasopharyngeal cancer, thymoma, rectal cancer, breast cancer, melanoma, kidney cancer, leukemia, and lymphoma.

4. The kit of claim 1, wherein the tumor is at least one selected from the group consisting of malignant mesothelioma, and non-small-cell lung cancer.

5. The kit of claim 1, wherein the specification comprises a description of usage, and wherein the description of usage directs a user to administer at least a portion of the formulation containing the ribonuclease and subsequently administer at least a portion of the formulation containing the artemisinin derivative.

6. The kit of claim 5, wherein the description of usage provides a waiting time between administration of the formulation containing the ribonuclease and administration of the formulation containing the artemisinin derivative.

7. The kit of claim 6, wherein the waiting time is between about 20 and 30 hours.

8. The kit of claim 5, wherein the description of usage further directs the user to administer at least a portion of a remaining formulation containing the ribonuclease and subsequently administer at least a portion of a remaining formulation containing the artemisinin derivative.

* * * * *